(12) United States Patent
Moussa et al.

(10) Patent No.: US 6,201,120 B1
(45) Date of Patent: Mar. 13, 2001

(54) SYNTHESIS OF 11-ARYL-5,6-DIHYDRO-11H-DIBENZ[B,E]AZEPINES

(75) Inventors: Adel M. Moussa, Burlington; Richard J. Lombardy, Waltham; Reem M. Haider, Malden, all of MA (US); Minghua Sun, Libertyville, IL (US)

(73) Assignee: Pharm-Eco Laboratories, Inc., Devens, MA (US)

( * ) Notice: Subject to any disclaimer, the term of this patent is extended or adjusted under 35 U.S.C. 154(b) by 0 days.

(21) Appl. No.: 09/370,819

(22) Filed: Aug. 9, 1999

Related U.S. Application Data

(62) Division of application No. 08/974,472, filed on Nov. 20, 1997, now Pat. No. 6,063,921.

(51) Int. Cl.[7] ........................ C07D 223/14; C07D 223/18

(52) U.S. Cl. .......................................... 540/576; 540/587

(58) Field of Search ...................... 540/587, 576

(56) References Cited

U.S. PATENT DOCUMENTS

| | | | |
|---|---|---|---|
| 3,402,171 | 9/1968 | Sternbach | 260/239.3 |
| 3,499,027 | 3/1970 | Saucy et al. | 260/471 |

FOREIGN PATENT DOCUMENTS

| | | |
|---|---|---|
| 558 800 | 2/1975 | (CH) . |
| 2 130 311 | 12/1971 | (DE) . |
| 2 130 312 | 12/1971 | (DE) . |
| 29 47 773 | 6/1980 | (DE) . |
| 30 15 025 | 11/1980 | (DE) . |
| 0 022 017 | 1/1981 | (EP) . |
| 0 135 770 A2 | 4/1985 | (EP) . |
| 0 471 516 A1 | 2/1992 | (EP) . |
| 0 567 026 A1 | 10/1993 | (EP) . |
| 0 645 378 A1 | 3/1995 | (EP) . |
| 1381678 | 3/1965 | (FR) . |

OTHER PUBLICATIONS

Sasakura, K. and Sugasawa T., "Synthesis of 11–Phenyl–5,6–Dihydro–11H–Dibenz(b,e)Azepine Derivatives," *Heterocycles*, 15 (1):421–425 (1981).

Brown, H.C. and Krishnamurthy S., "Boranes for Organic Reduction—A Forty–Year Odyssey[1]," *Aldrichimica Acta*, 12 (1):3–11 (1979).

Kisel, V.M., et al., "Condensed Isoquinolines. Part 6. Synthesis of 5–Aryl–7,12–Dihydroisoquino[2,3–a] Quinazolinium Salts," *Chemistry of Heterocyclic Compounds* 31 (5):586–587 (1995).

Greuter, H. and Schmid, H., "Intramoleculare Additionen α–lithiierter Amide; eine neue Synthese von 2–aryl– und 2–Vinylindolen," *Helvetica Chimica Acta* 57:281–286 (1974).

Molina, P., et al., "New Methodology for the Preparation of Pyrrole and Indole Derivatives via Iminophosphoranes: Synthesis of Pyrrolo[1,2–a]Quinoxalines, Indolo[3,2–c] Quinolines and Indolo[1,2–c]Quinazolines," *Tetrahedron 46* (3):1063–1078 (1990).

Bogatskii, A.V., et al., "Enzymatic Synthesis of 2–(Acylamino–R–Propionylamido)Benzophenones," *Doklady Chemistry 252* :280–282 (1980).

(List continued on next page.)

*Primary Examiner*—Richard L. Raymond
*Assistant Examiner*—Brenda Coleman
(74) *Attorney, Agent, or Firm*—Hamilton, Brook, Smith & Reynolds, P.C.

(57) ABSTRACT

Disclosed is a three step synthesis of 11-aryl-5,6-dihydro-11H-dibenz[b,e]azepines from a 2-aminobenzophenone represented by the following structural formula:

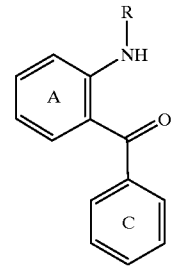

and a starting material represented by the following structural formula:

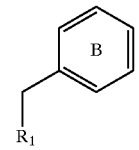

Phenyl Ring A, Phenyl Ring B and Phenyl Ring C are independently unsubstituted or substituted with one, two or three substituents. Each substituent on Phenyl Ring A, Phenyl Ring B and Phenyl Ring C is independently chosen.

R is —H, a aliphatic group, a substituted aliphatic group, an aryl group, a substituted aryl group, —C(O)—R', —C(O)—H, —C(O)—NHR', —S(O)$_2$R', —C(O)—C(O)—R', —C(O)—C(O)—H, —C(S)—R', —C(S)—H, —C(O)—OR', —C(S)—OR', —C(O)—SR', —C(S)—SR', —C(O)—NR'$_2$ or —C(O)—C(S)—R'. R' is an aliphatic group, a substituted aliphatic group, an aryl group or a substituted aryl group.

R$_1$ is a leaving group.

The present invention also includes novel compounds which are intermediates in the preparation of 11-aryl-5,6-dihydro-11H-dibenz[b,e]azepines.

9 Claims, 7 Drawing Sheets

OTHER PUBLICATIONS

Bogatskii, A.V., et al., "Synthesis and Pharmacological Properties of 6–Aryl–1,2,3,4–Tetrahydro–1,5–Benzodiazocin–2–Ones," *Pharm. Chem. J.* *14*(8):540–542 (1980).

Nishino, H. and Kurosawa, K., "Reaction of Secondary Aromatic Amines with Manganese(III) Acetate," *Bull. Chem. Soc. Jpn.* *56*(6):1682–1687 (1983).

Wagner, P.J. and Cao, Q., "Photocyclization of Ortho–Benzoyl N–Alkylanilinium Ions," *Tetrahedron Letters* *32* (32):3915–3918 (1991).

SYNTHESIS OF 11-ARYL-5,6-DIHYDRO-11H-DIBENZ[B,E]AZEPINES

RELATED APPLICATION

This application is a divisional application of U.S. Ser. No. 08/974,472, filed Nov. 20, 1997 now U.S. Pat. No. 6,063,921, the entire teachings of which are incorporated herein by reference.

BACKGROUND OF THE INVENTION

Compounds which inhibit the $Ca^{2+}$-activated potassium channel (Gardos channel) of cells are useful in the treatment of a wide variety of diseases. For example, Sickle Cell Anemia can be treated with compounds which inhibit the $Ca^{2+}$-activated potassium channel of erythrocytes (Stuart et al., *J. Haematol.* 86:820 (1994). In addition, agents capable of inhibiting $Ca^{2+}$-activated potassium channels have been shown to be useful in the treatment of arteriosclerosis (U.S. Pat. No. 5,358,959 to Halperin et al.) Moreover, cell proliferation is dependent on the regulated movement of ions across various cellular compartments, including activation of $Ca^{2+}$-activated potassium channels (Magni et al., *J. Biol. Chem.* 261:9321 (1991)). Thus, agents which inhibit Ca $^{2+}$-activated potassium channels can be used in the treatment of proliferative diseases, including cancer, blood vessel proliferative disorders, fibrotic disorders and arteriosclerotic conditions.

SUMMARY OF THE INVENTION

The present invention is a method of preparing 11-aryl-5,6-dihydro-11H-dibenz[b,e]azepines. The present invention also includes novel compounds which are intermediates in the preparation of 11-aryl-5,6-dihydro-11H-dibenz[b,e] azepines and methods of preparing the intermediates.

In one embodiment, the present invention is a method of preparing an 11-aryl-5,6-dihydro-11H-dibenz[b,e]azepine represented by Structural Formula (I):

(I)

Phenyl Ring A, Phenyl Ring B and Phenyl Ring C are independently unsubstituted or substituted with one, two or three substituents. Each substituent on the 11-aryl-5,6-dihydro-11H-dibenzo[b,e]azepine is independently chosen.

R is —H, an aliphatic group, a substituted aliphatic group, an aryl group, a substituted aryl group, —C(O)—R', —C(O)—H, —C(O)—NHR', —S(O)$_2$R', —C(O)—C(O)—R', —C(O)—C(O)—H, —C(S)—R', —C(S)—H, —C(O)—OR', —C(S)—OR', —C(O)—SR', —C(S)—SR', —C(O)—NR'$_2$ or —C(O)—C(S)—R'. R' is an aliphatic group, a substituted aliphatic group, an aryl group or a substituted aryl group.

The method of preparing an 11-aryl-5,6-dihydro-11H-dibenz[b,e]azepine represented by Structural Formula (I) comprises a first step in which a base, a substituted 2-aminobenzophenone and a starting material are reacted to form a diphenyl ketone. The 2-aminobenzophenone, the starting material and the diphenyl ketone are represented by Structural Formulas (II), (III) and (IV), respectively:

(II)

(III)

(IV)

In Structural Formulas (II)–(IV), R$_1$ is a leaving group and R, Phenyl Ring A, Phenyl Ring B, and Phenyl Ring C are as described for Structural Formula (I).

The method of preparing an 11-aryl-5,6-dihydro-11H-dibenz[b,e]azepine represented by Structural Formula (I) comprises a second step in which the diphenyl ketone represented by Structural Formula (IV) is reacted with a ketone reducing agent to form an intermediate represented by Structural Formula (V):

(V)

In Structural Formula (V), R, Phenyl Ring A, Phenyl Ring B, and Phenyl Ring C are as described for Structural Formula (I).

The method of preparing an 11-aryl-5,6-dihydro-11H-dibenz[b,e]azepine represented by Structural Formula (I) comprises a third step in which the intermediate represented by Structural Formula (V) is reacted with one or more Lewis acids to form the 11-aryl-5,6-dihydro-11H-dibenz[b,e]azepine.

Another embodiment of the present invention is a method of forming a diphenyl ketone represented by Structural Formula (IV). The method comprises reacting a base, a 2-aminobenzophenone represented by Structural Formula (II) and a starting material represented by Structural Formula (III) to form the diphenyl ketone.

Another embodiment of the present invention is a method of forming an intermediate represented by Structural Formula (V). The method comprises reacting a diphenyl ketone represented by Structural Formula (IV) with a ketone reducing agent to form said intermediate.

Another embodiment of the present invention is a method of forming an intermediate represented by Structural Formula (V). The method comprises a first step of reacting a base, a 2-aminobenzophenone represented by Structural Formula (II) and a starting material represented by Structural Formula (III) to form a diphenyl ketone represented by Structural Formula (IV) and a second step of reacting the diphenyl ketone with a ketone reducing agent to form the intermediate represented by Structural Formula (V).

Another embodiment of the present invention is a method of forming a 11-aryl-5,6-dihydro-11H-dibenz[b,e]azepine from a diphenyl methanol. The 11-aryl-5,6-dihydro-11H-dibenz[b,e]azepine and the diphenyl methanol are represented by Structural Formulas (I) and (V), respectively, with the provisos that 1) at least one of Ring A, Ring B or Ring C is substituted; 2) when Ring B and Ring C are unsubstituted, Ring A is not substituted with —Cl para to the carbon atom bonded to the amino group; and 3) when Ring A and Ring C are unsubstituted, Ring B is not substituted with —OCH$_3$ at positions three, four and five with respect to the carbon bonded to the methyl amino group. Thus, 11-aryl-5,6-dihydro-11H-dibenz[b,e]azepines and diphenyl methanols represented by Structural Formulas (VI)–(VIII) and (IX)–(XI), respectively, are excluded:

(VI)

(VII)

(VIII)

(IX)

(X)

(XI)

Another embodiment of the present invention is a method of forming a 11-aryl-5,6-dihydro-11H-dibenz[b,e]azepine represented by Structural Formula (I). The method comprises a first step of reacting a ketone reducing agent with a diphenyl ketone represented by Structural Formula (IV) to form an intermediate represented by Structural Formula (V) and reacting the intermediate with a Lewis acid to form the 11-aryl-5,6-dihydro-11H-dibenz[b,e]azepine.

Another embodiment of the present invention is a compound represented by Structural Formula (IV). Yet another embodiment of the present invention is a compound represented by Structural Formula (V) with the proviso that the compound is not represented by Structural Formulas (IX), (X) or (XI).

It is reported in co-pending U.S. patent applications that 11-aryl-5,6-dihydro-11H-dibenz[b,e]azepines inhibit Ca$^{2+}$- activated potassium channels and are therefore useful in treating sickle cell anemia, asteriosclerosis and proliferative diseases. The methods described herein can be used to prepare 11-aryl-5,6-dihydro-11H-dibenz[b,e]azepine in three reaction steps in overall yields of between about 10% and 35%. The starting materials and reagents are readily available and inexpensive. Thus, the present invention is an efficient and cost-effective method of preparing pharmacologically active agents useful in the treating sickle cell anemia, proliferative diseases such as cancer, blood vessel proliferative disorders, fibrotic disorders and arteriosclerotic conditions.

BRIEF DESCRIPTION OF THE FIGURES

FIGS. 2A–2I-1 show structural formulas of exemplary compounds which have been prepared by the methods of the present invention.

DETAILED DESCRIPTION OF THE INVENTION

Figure 1:
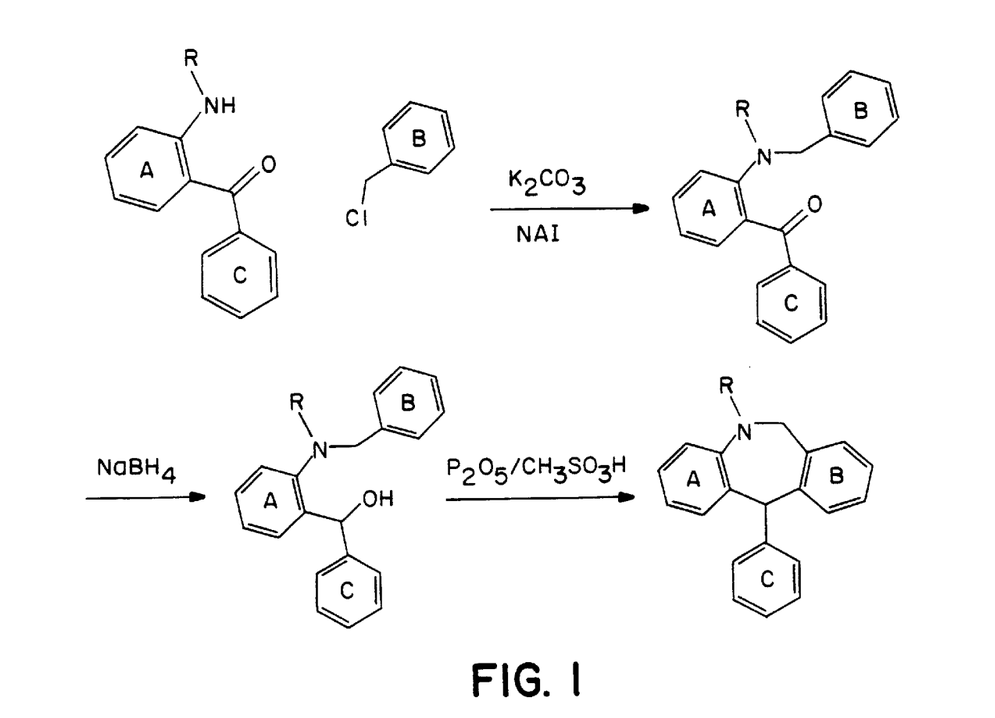
FIG. 1 is a schematic showing the disclosed method of preparing 11-aryl-5,6-dihydro-11H-dibenz[b,e]azepines.
Figure 2A:
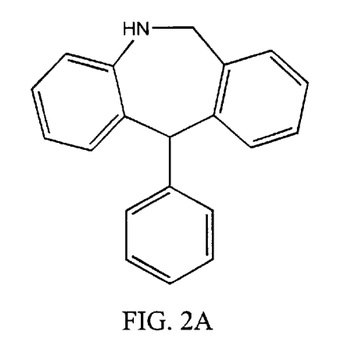
Figure 2A:
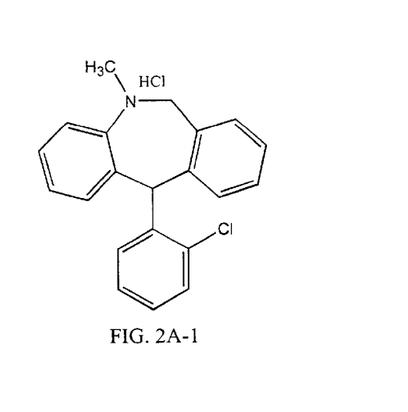
Figure 2B:
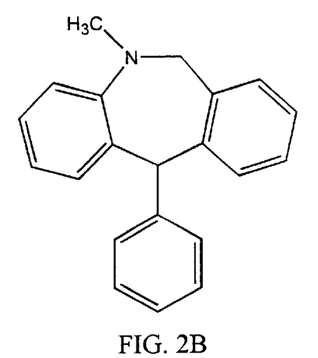
Figure 2B:
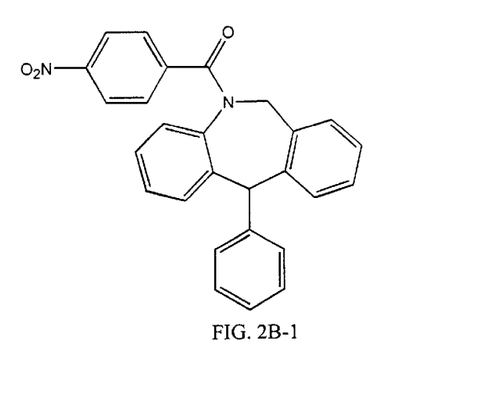
Figure 2C:
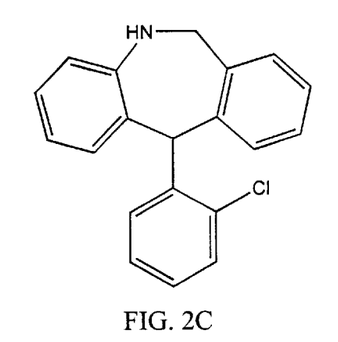
Figure 2C:
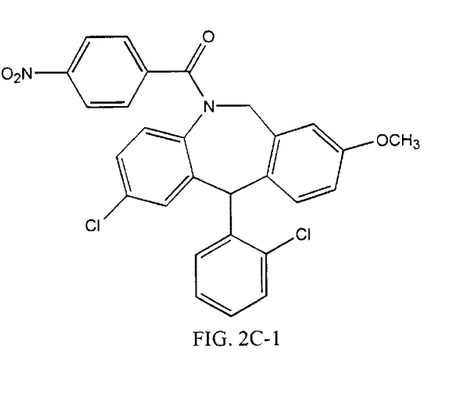
Figure 2D:
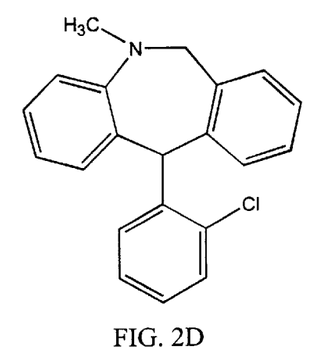
Figure 2D:
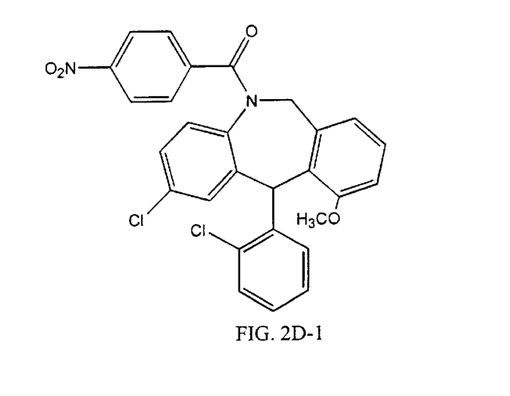
Figure 2E:
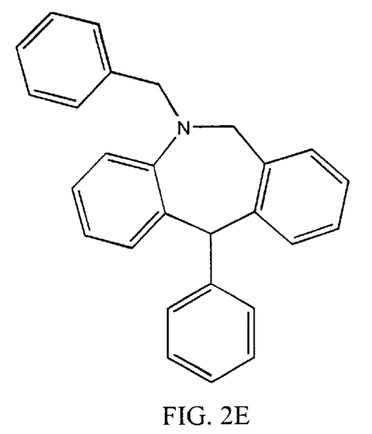
Figure 2E:
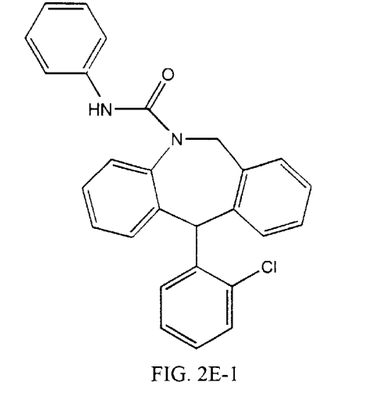
Figure 2F:
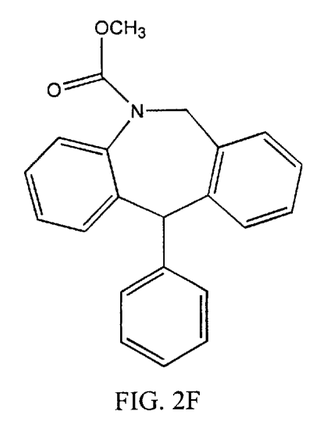
Figure 2F:
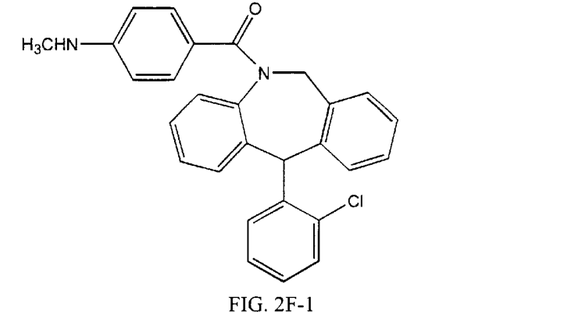
Figure 2G:
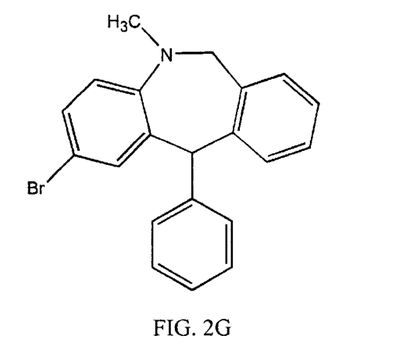
Figure 2G:
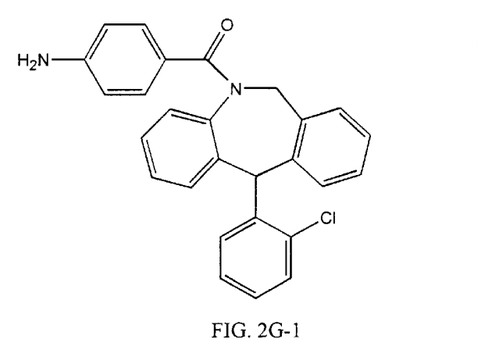
Figure 2H:
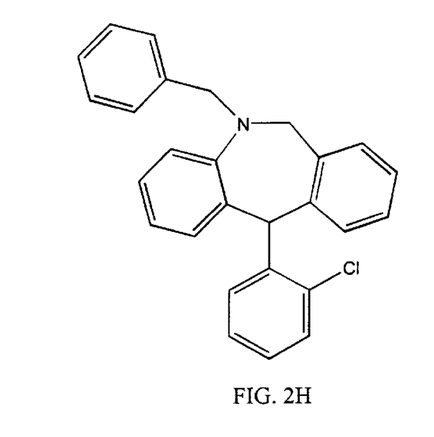
Figure 2H:
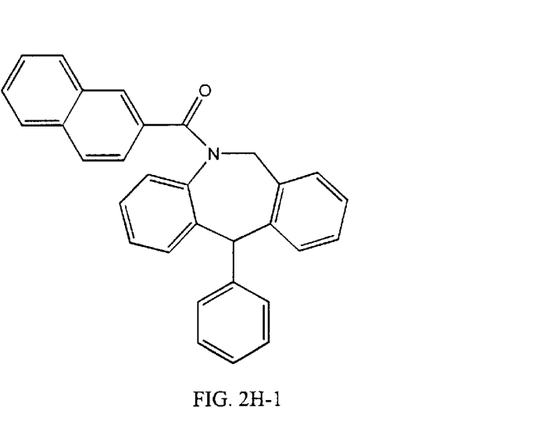
Figure 2I:
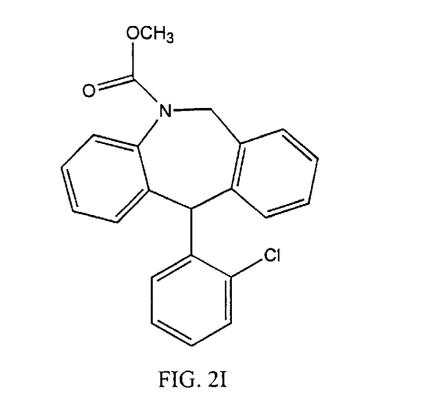
Figure 2I:
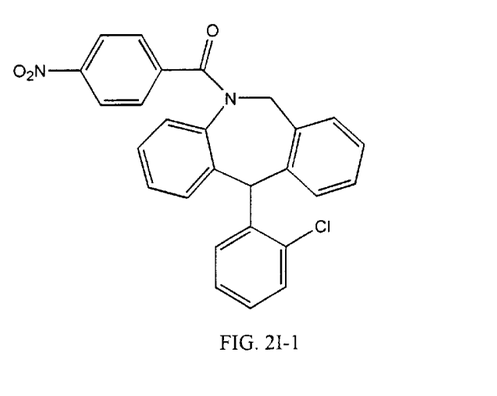
Figure 2J:
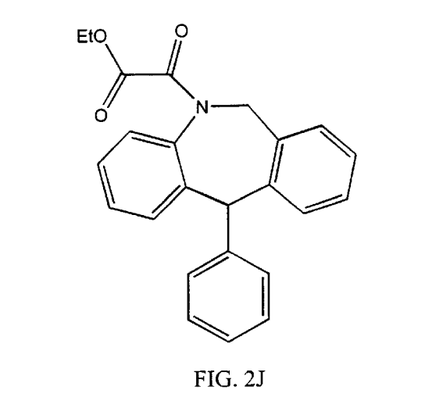
Figure 2K:
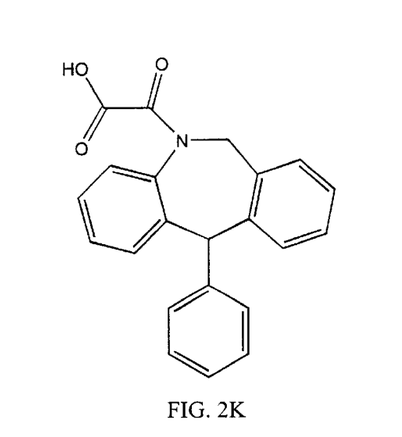
Figure 2L:
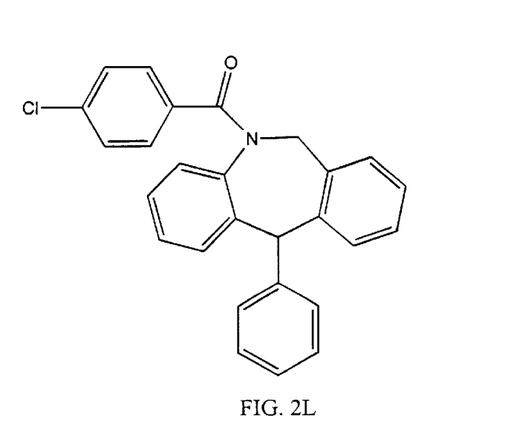
Figure 2M:
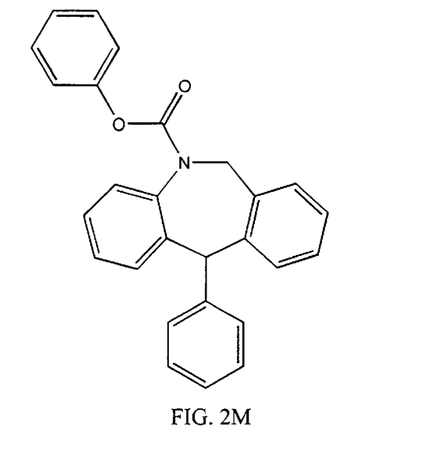
Figure 2N:
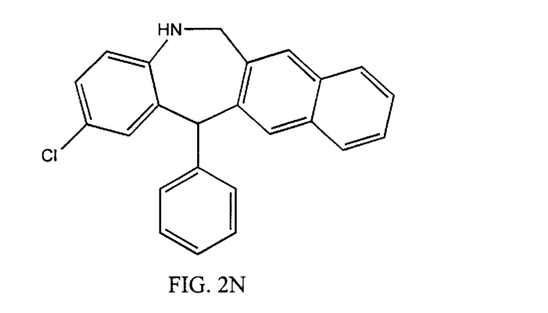
Figure 2O:
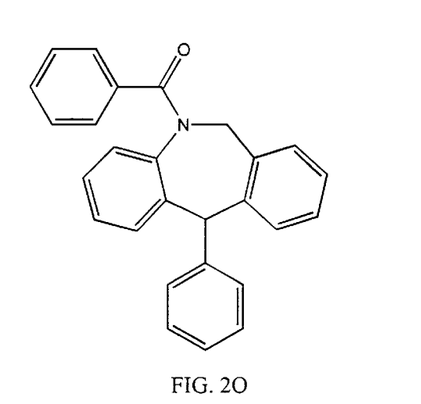
Figure 2P:
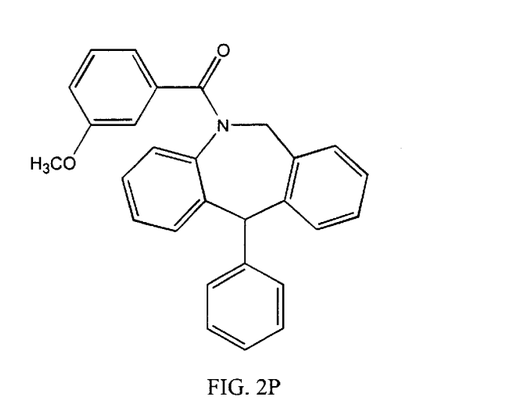
Figure 2Q:
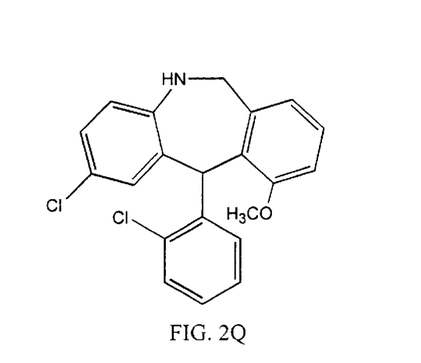
Figure 2R:
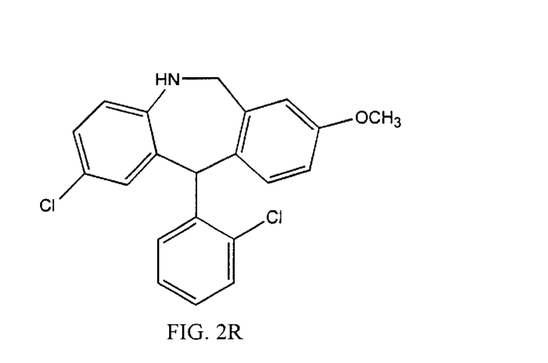
Figure 2S:
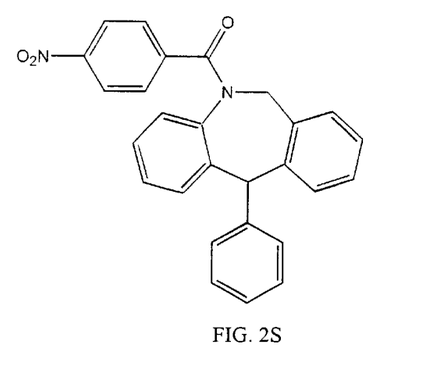
Figure 2T:
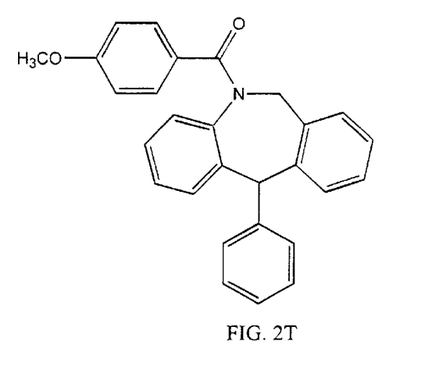
Figure 2U:
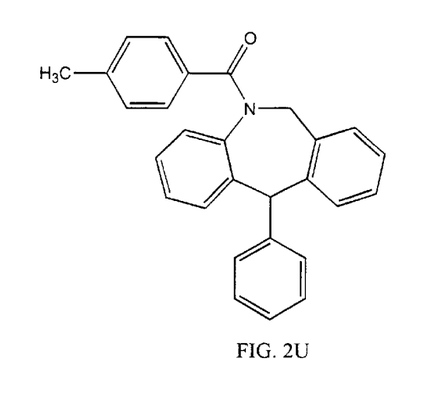
Figure 2V:
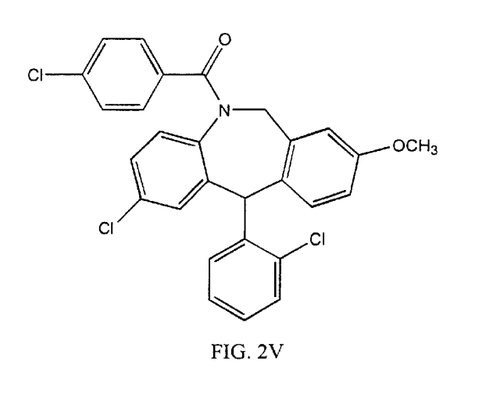
Figure 2W:
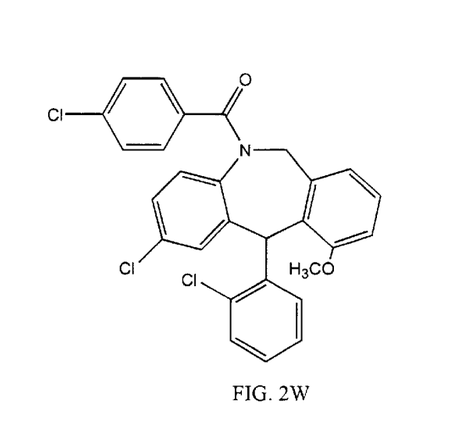
Figure 2X:
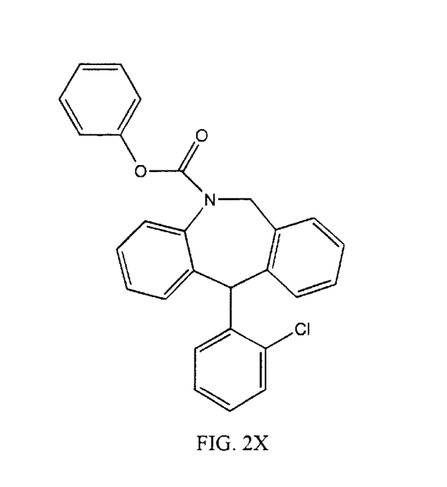
Figure 2Y:
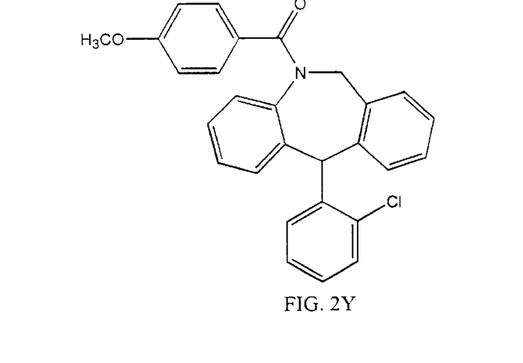
Figure 2Z:
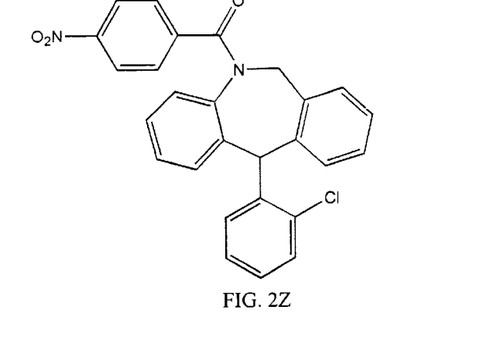

The features and details of the invention will now be more particularly described below and pointed out in the claims. It will be understood that the particular embodiments of the invention are shown by way of illustration and not as limitations of the invention. The principal features of this invention can be employed in various embodiments without departing from the scope of the invention.

Suitable substituents for Phenyl Ring A, Phenyl Ring B and Phenyl Ring C and suitable groups for R include those which are compatible with the reactions and reagents used in the methods of the present invention. A substituent or group is compatible with a reaction when the substituent or group does not significantly reduce the yield of the reaction and does not cause a significant amount of side reactions. The reagents used in the methods of the present invention are well known in the field of organic chemistry. Thus, the skilled person will readily recognize those groups and substituents which are not compatible with these reagents, and, as a consequence, will also recognize those groups and substituents which are not compatible with a reaction used in the methods disclosed herein.

Examples of groups and substituents which are not compatible with the conversion of a diphenyl ketone represented by Structural Formula (IV) to a diphenyl methanol represented by Structural Formula (V) include acidic groups such as alcohols, phenols, carboxylic acids and sulfonic acids. Functional groups such as ketones, imines, aldehydes and, in certain cases, esters, can also react with ketone reducing agents. Functional groups which can act as Lewis bases, for example, amines, alcohols and phenols, react with Lewis acids and are therefore incompatible with the ring closure reaction in which a diphenyl methanol represented by Structural Formula (V) is converted to a 11-aryl-5,6-dihydro-11H-dibenz[b,e]azepine represented by Structural Formula (I).

Although certain functional groups, for example, those described in the previous paragraphs, are not compatible with at least one reaction used in the method of the present invention, these functional groups can be present if they are first converted to a suitable protected form. The protecting group can then be removed after the reaction with which the functional group is incompatible is performed. Protecting groups are well known in the art and are described in, for example, Greene and Wuts, "Protective Groups in Organic Synthesis", John Wiley & Sons (1991), the entire teachings of which are incorporated into this application by reference. The skilled artisan can select, using no more than routine experimentation, suitable protecting groups for use in the disclosed synthesis as well as conditions for applying and removing the protecting groups.

Examples of suitable substituents for Phenyl Ring A, Phenyl Ring B and Phenyl Ring C include aliphatic groups, substituted aliphatic groups, aryl groups, substituted aryl groups, halogens (e.g., fluoro, chloro, bromo and iodo), halogenated alkyl groups (e.g., trihalomethyl) nitro, nitrile, —CONH(aliphatic group, substituted aliphatic group, aryl group or substituted aryl group), —CON(aliphatic group, substituted aliphatic group, aryl group or substituted aryl group)$_2$, —O—(aliphatic group, substituted aliphatic group, aryl group or substituted aryl group), —N(aliphatic group, substituted aliphatic group, aryl group or substituted aryl group)$_2$, —S(aliphatic group, substituted aliphatic group, aryl group or substituted aryl group), —S(O)(aliphatic group, substituted aliphatic group, aryl group or substituted aryl group), —S(O)$_2$(aliphatic group, substituted aliphatic group, aryl group or substituted aryl group). Also included are aryl groups, for example, a phenyl group, which are fused onto Phenyl Ring A, Phenyl Ring B or Phenyl Ring C. Ring B is preferably substituted meta to the carbon atom bonded to the aminomethyl group with electron donating substituents. Examples include alkoxy groups, —Cl, —Br, —I, aliphatic groups, substituted aliphatic groups, aryl groups, substituted aryl group, —N(aliphatic group)$_2$ and —N(substituted aliphatic group)$_2$, —N(aryl group)$_2$ and —N(substituted aryl group)$_2$, —NH—CO(aliphatic group), —NH—CO(substituted aliphatic group), —NH—CO(aryl group) and —NH—CO(substituted aryl group).

Examples of suitable values for R include —H, an aliphatic group, a substituted aliphatic group, an aryl group, a substituted aryl group, —C(O)—R', —C(O)—H, —C(O)—NHR', —S(O)$_2$R', —C(O)—C(O)—R', —C(O)—C(O)—H, —C(S)—R', —C(S)—H, —C(O)—OR', —C(S)—OR', —C(O)—SR', —C(S)—SR', —C(O)—NR'$_2$ or —C(O)—C(S)—R', wherein R' is an aliphatic group, a substituted aliphatic group, an aryl group or a substituted aryl group. R' is preferably a C1–C8 straight or branched chain alkyl group, a phenyl group, a substituted phenyl group, a naphthyl group or a substituted naphthyl group.

Phenyl Ring A, Phenyl Ring B and Phenyl Ring C are independently unsubstituted or substituted with one, two or three substituents which are independently chosen. Thus, the number of substituents and the substitution pattern on one of these phenyl rings are independent of the number of substituents and substitution patterns on the other two rings. In addition, the selection of each substituent is independent of the other substituents on the same phenyl ring or the other two phenyl rings.

Preferably, Phenyl Ring A, Phenyl Ring B and Phenyl Ring C in Structural Formulas (I)–(V) are independently unsubstituted or monosubstituted. Thus, the substitution pattern and selection of the substituent on a phenyl ring is independent of the substitution patterns and selection of substituents on the other two phenyl rings. More preferably, the 11-aryl-5,6-dihydro-11H-dibenz[b,e]azepine represented by Structural Formula (I), the 2-aminobenzophenone represented by Structural Formula (II), the starting material, represented by Structural Formula (III), the diphenyl ketone represented by Structural Formula (IV) and the diphenyl methanol represented by Structural Formula (V) are represented by Structural Formulas (XII)–(XVI), respectively:

In Structural Formulas (XII)–(XVI):
R is —H, —CH$_3$, benzyl, —C(O)—OCH$_3$, —C(O)—C(O)—OH, —C(O)—C(O)—OCH$_2$CH$_3$, para-chlorobenzoyl, —C(O)—O—(phenyl), benzoyl, meta-methoxybenzoyl, para-nitrobenzoyl, para-methoxybenzoyl, para-methylbenzoyl, para-chlorobenzoyl, naphthoyl, —C(O)—NH—(phenyl), para-methylaminobenizoyl, para-aminobenzoyl or —C(O)—NH—(4—NO$_2$-phenyl);

R$_1$ is a halide;
R$_2$ is —H, —F, —Cl, —Br or —I;
R$_3$ and R$_5$ are independently —H, —OCH$_3$, —OCH$_2$CH$_3$, —F, —Cl, —Br or —I;
R$_4$ is —H or, taken together with R$_3$ and the carbon atoms to which R$_3$ and R$_4$ are bonded, a phenyl group; and
R$_6$ is —H, —F, —Cl, —Br or —I.

As used herein, aliphatic groups include straight chained, branched or cyclic C$_1$–C$_8$ hydrocarbons which are completely saturated or which contain one or more units of unsaturation.

Aryl groups include carbocyclic aromatic groups such as phenyl, 1-naphthyl, 2-naphthyl, 1-anthracyl and 2-anthacyl, and heterocyclic aromatic groups such as N-imidazolyl, 2-imidazole, 2-thienyl, 3-thienyl, 2-furanyl, 3-furanyl, 2-pyridyl, 3-pyridyl, 4-pyridyl, 2-pyrimidy, 4-pyrimidyl, 2-pyranyl, 3-pyranyl, 3-pyrazolyl, 4-pyrazolyl, 5-pyrazolyl, 2-pyrazinyl, 2-thiazole, 4-thiazole, 5-thiazole, 2-oxazolyl, 4-oxazolyl and 5-oxazolyl.

Aryl groups also include fused polycyclic aromatic ring systems in which a carbocyclic aromatic ring or heteroaryl ring is fused to one or more other heteroaryl rings. Examples include 2-benzothienyl, 3-benzothienyl, 2-benzofuranyl, 3-benzofuranyl, 2-indolyl, 3-indolyl, 2-quinolinyl, 3-quinolinyl, 2-benzothiazole, 2-benzooxazole, 2-benzimidazole, 2-quinolinyl, 3-quinolinyl, 1-isoquinolinyl, 3-quinolinyl, 1-isoindolyl, 3-isoindolyl, and acridinyl.

Suitable substituents for an aryl group or an aliphatic group are those which are compatible with reactions and reagents used in the methods of the present invention, including those discussed hereinabove for Phenyl Ring A, Phenyl Ring B and Phenyl Ring C.

With respect to the reaction of the 2-aminobenzophenone and starting material to form the diphenylketone represented by Structural Formula (IV) (the "alkylation reaction"), "leaving group" refers to a functional group which can be facilely displaced with a nucleophilic reagent such as an amine. Leaving groups are generally functional groups which are strongly electron withdrawing and include —Cl, —Br—, —I and sulfonate esters such as mesylates, benzenesulfonate, tosylate, brosylate and nitrobenzene-sulfonate. Preferred leaving groups are —Cl or —Br, in which case an iodide salt such as sodium iodide or a tetraalkyl iodide is generally included in the reaction mixture. About one to about five equivalents of the iodide salt with respect to starting material, preferably about 1.0 to about 1.2 equivalents, is used.

Suitable bases for the alkylation reaction include carbonate bases, hydroxide bases, alkoxide bases, hydride bases, amide bases and alkyl lithium bases. Generally, with respect to the 2-aminobenzophenone, about one to about five equivalents of base are used, preferably about 1.5 to about 2.5 equivalents. Carbonate bases, for example, potassium carbonate, are preferred. Equimolar amounts of starting material and 2-aminobenzophenone are generally used. However, excesses as large as one to two fold of either reactant can be used.

Polar organic solvents are generally used for the alkylation reaction, Examples include acetonitrile, nitromethane, methylene chloride, tetrahydrofuran, 1,4-dioxane, dimethylformamide and dimethoxyethane. Acetonitrile is preferred. The alkylation is performed at concentrations, for example, ranging from about 0.01 M to about 5.0 M, preferably from about 0.1 M to about 1.0 M. The reaction temperature ranges, for example, from about room temperature to about 150° C., preferably from about 90° C. to about 110° C.

An example of specific conditions suitable for performing the alkylation reaction is provided in Example 1, infra.

Suitable reagents for reducing ketone groups are well known in the art and include, for example, hydride reducing agents such as sodium borohydride, lithium aluminum hydride, lithium borohydride, alkali metal trialkyl borohydrides and alkali metal trialkoxy aluminum hydides. Conditions suitable for reducing a ketone to an alcohol with hydride reducing agents are well known in the art and are described, for example, in Brown et al., *Aldrichimica Acta* 12:3 (1979) and references cited therein, the entire teachings of which are incorporated herein by reference. Borane reagents such as diborane tetrahydrofuran, diborane dimethyl sulfide, alkyl boranes and dialkyl boranes can also be used as ketone reducing agents. Conditions suitable for reducing a ketone to an alcohol with borane reagents are well known in the a it and are described, for example, in Lane, *Aldrichimica Acta* 10:41 (1977) and references cited therein, the entire teachings of which are incorporated herein by reference. There are many other reagents suitable for reducing a ketone to alcohol which are known in the art. It is to be understood that these reagents are also encompassed by the term "ketone reducing agent".

With respect to the reduction of the diphenyl ketone represented by Structural Formula (IV) to the diphenyl methanol represented by Structural Formula (V) (the "reduction"), sodium borohydride is a preferred ketone reducing reagent. The reduction with sodium borohydride is typically performed in an etheral solvent, such as diethyl ether, tetrahydrofuran, glyme or 1,4-dioxane, an alcoholic solvent such as methanol, ethanol or iso-propanol, or mixtures thereof. The reduction with other hydride reducing agents is generally performed in etheral solvents. Generally, about 0.75 to about 3.0 equivalents of reducing agent with respect to diphenylketone are used, preferably about 0.9 to about 1.25 equivalents. The reduction is performed at concentrations, for example, ranging from about 0.01 M to about 5.0 M, preferably from about 0.1 M to about 1.0 M. The reaction temperature ranges, for example, from about 0° to about 50° C., preferably at ambient temperature.

Specific conditions for performing the reduction are provided in Example 2.

Lewis acids suitable for use in the preparation of 11-aryl-5,6-dihydro-11H-dibenz[b,e]azepine represented by Structural Formula (I) from diphenylmethanols represented by Structural Formula (V) (the "ring closure reaction") are those which can bring about the ionization of secondary alcohols in solution. Examples include sulfonic acids (e.g., methanesulfonic acid, benzesulfonic acid, toluenesulfonic acid, triflic acid and chlorosulfonic acid), sulfuric acid, phosphorus pentoxide, polyphosphoric acid and mixtures thereof. The reaction is typically performed in a polar organic solvent such as chloroform, methylene chloride, acetonitrile, nitromethane or 1,4-dioxane, preferably methylene chloride, at temperatures ranging from about 0° C. to about 50° C., preferably at ambient temperature. Excesses up to about ten to about fifteen fold of Lewis acid relative to the diphenyl alcohol can be used. Preferebly the Lewis acid is a mixture of phosphorus pentoxide and methansulfonic acid with about 4.5 to about 5.5 equivalents of each relative to the diphenyl alcohol. Specific conditions for performing the ring closure reaction are provided in Example 3.

All reactions can be monitored for completion by methods known in the art, for example, by thin layer chromatography, high pressure liquid chromatography or gas chromatography.

When preparing 11-aryl-5,6-dihydro-11H-dibenz[b,e] azepine represented by Structural Formula (I) in which R is —C(O)—R', —C(O)—H, —C(O)—NHR', —S(O)$_2$R', —C(O)—C(O)—R', —C(O)—C(O)—H, —C(S)—R', —C(S)—H, —C(O)—OR', —C(S)—OR', —C(O)—SR', —C(S)—SR', —C(O)—NR'$_2$ or —C(O)—C(S)—R', it is preferred to first prepare the corresponding 11-aryl-5,6-dihydro-11H-dibenz[b,e]azepine in which R is —H and then add the desired group to the secondary amine. Methods of adding these groups to secondary amines are well known in the art. Specific examples are provided in co-pending application "SUBSTITUTED 11-PHENYL DIBENZAZEPINE COMPOUNDS AND ANALOGUES THEREOF USEFUL FOR THE TREATMENT OR PREVENTION OF SICKLE CELL DISEASE OR DISEASES CHARACTERIZED BY ABNORMAL CELL PROLIFERATION", the entire teachings of which have been incorporated herein by reference.

Also included in the present invention are salts of the compounds represented by Structural Formulas (IV) and (V). Salts of an amine can be obtained, for example, by reacting with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like.

The invention is illustrated by the following examples which are not intended to be limiting in any way.

EXEMPLIFICATION

Example 1

Synthesis of Diphenyl Ketones Represented By Structural Formula (IV)

A mixture of an appropriately substituted 2-aminobenzophenone (1 equivalent), an appropriately substituted benzyl chloride (1 equivalent), potassium carbonate (2 equivalents) and sodium iodide (1 equivalent) in acetonitrile was refluxed for 12 hours. The reaction mixture was cooled to room temperature and water added. The mixture was extracted with ethyl acetate. The combined ethyl acetate extracts were washed with water then dried over sodium sulfate. Evaporation of the solvent followed by column chromatography gave the diphenyl ketone in about 55–80% yield.

Example 2

Synthesis of Diphenyl Methanols Represented by Structural Formula (V) from Diphenyl Ketones Represented by Structural Formula (IV)

The diphenyl ketone (1 equivalent) was dissolved in a 3:1 mixture of tetrahydrofuran:methanol. Sodium borohydride (10 equivalents) was slowly added and the reaction mixture was stirred at room temperature for 12 hours. The reaction was quenched by adding 2 N aqueous hydrochloric acid solution. The reaction mixture was neutralized by adding 4 N aqueous sodium hydroxide solution followed by extraction with ethyl acetate. The combined ethyl acetate extracts were dried over sodium sulfate. Evaporation of the solvent followed by column chromatography gave the diphenyl methanol in about 40–60% yield.

Example 3

Preparation of 11-Aryl-5,6-Dihydro-11H-Dibenzo[b,e] azepines Represented by Structural Formula (I) from Diphenyl Methanols Represented by Structural Formula (D)

A mixture of substituted N-alkyl-2-amino-benzylalcohol derivative (1 equivalent), phosphorous pentoxide (5 equivalents) and methanesulfonic acid (5 equivalents) in dichloromethane was stirred at room temperature for 12 hours. The mixture was neutralized by adding aqueous sodium carbonate and then extracted with dichloromethane. The organic solution was dried over sodium sulfate. Evaporation of the solvent followed by column chromatography gave the substituted 11-aryl-5,6-dihydro-11H-dibenz(b,e) azepine derivative in about 45–70% yield.

EQUIVALENTS

While this invention has been particularly shown and described with references to preferred embodiments thereof, it will be understood by those skilled in the art that various changes in form and details may be made therein without departing from the spirit and scope of the invention as defined by the appended claims. Those skilled in the art will recognize or be able to ascertain using no more than routine experimentation, many equivalents to the specific embodiments of the invention described specifically herein. Such equivalents are intended to be encompassed in the scope of the claims.

What is claimed is:

1. A method of preparing an 11-aryl-5,6-dihydro-11H-dibenz[b,e]azepine represented by the following structural formula:

wherein:
Phenyl Ring A, Phenyl Ring B and Phenyl Ring C are independently unsubstituted or substituted with one, two or three substituents, wherein each substituent is independently chosen with the provisos that 1) at least one of Ring A, Ring B or Ring C is substituted; 2) when Ring B and Ring C are unsubstituted, Ring A is not substituted with —Cl para to the carbon atom bonded to the nitrogen atom; and 3) when Ring A and Ring C are unsubstituted, Ring B is not substituted with —OCH$_3$ at positions three, four and five with respect to the carbon bonded to the methyl amino group; and R is —H, an aliphatic group, a substituted aliphatic group, an aryl group, a substituted aryl group, —C(O)—R', —C(O)—H, —C(O)—NR'$_2$, —C(O)—NHR', —S(O)$_2$R', —C(O)—C(O)—R', —C(O)—C(O)—H, —C(O)—C(O)—OH, —C(O)—C(O)—OCH$_2$CH$_3$—C(S)—R', —C(S)—H, —C(O)—OR', —C(S)—OR', —C(O)—SR', —C(S)—SR', or —C(O)—C(S)—NR'$_2$, wherein R' is an aliphatic group, a substituted aliphatic group, an aryl group or a substituted aryl group;

said method comprising reacting one or more Lewis acids with a diphenyl methanol represented by the following structural formula:

2. The method of claim 1 wherein Phenyl Ring A, Phenyl Ring B and Phenyl Ring C are independently unsubstituted or monosubstituted.

3. The method of claim 2 wherein the Lewis acid is sulfuric acid, a sulfonic acid, phosphorus pentoxide, polyphosphoric acid or a mixture thereof.

4. The method of claim 2 wherein the Lewis acid is about a 1:1 mixture of methanesulfonic acid and phosphorus pentoxide.

5. The method of claim 2 wherein the diphenyl methanol is represented by the following structural formula:

wherein:
R is —H, —CH$_3$, benzyl, —C(O)—OCH$_3$, —C(O)—C(O)—OH, —C(O)—C(O)—OCH$_2$CH$_3$, para-chlorobenzoyl, —C(O)—O—(phenyl), benzoyl, meta-methoxybenzoyl, para-nitrobenzoyl, para-methoxybenzoyl, para-methylbenzoyl, para-chlorobenzoyl, naphthoyl, —C(O)—NH—(phenyl), para-methylaminobenzoyl, para-aminobenzoyl or —C(O)—NH—(4—NO$_2$-phenyl);

R$_2$ is —H, —F, —Cl, —Br or —I;

R$_3$ and R$_5$ are independently —H, —OCH$_3$, —OCH$_2$CH$_3$, —F, —Cl, —Br or —I;

R$_4$ is —H or, taken together with R$_3$ and the carbon atoms to which R$_3$ and R$_4$ are bonded, a phenyl group; and R$_6$ is —H, —F, —Cl, —Br or —I.

6. A method of preparing an 11-aryl-5,6-dihydro-11H-dibenz[b,e]azepine represented by the following structural formula:

wherein:
Phenyl Ring A, Phenyl Ring B and Phenyl Ring C are independently unsubstituted or substituted with one, two or three substituents, wherein each substituent is independently chosen; and R is —H, an aliphatic group, a substituted aliphatic group, an aryl group, a substituted aryl group, —C(O)—R', —C(O)—H, —C(O)—NR'$_2$, —C(O)—NHR', —S(O)$_2$R', —C(O)—C(O)—R', —C(O)—C(O)—H, —C(O)—C(O)—OH, —C(O)—C(O)—OCH$_2$CH$_3$, —C(S)—R', —C(S)—H, —C(O) —OR', —C(S)—OR', —C(O)—SR', —C(S)—SR', or —C(O)—C(S)—NR'$_2$, wherein R' is an aliphatic group, a substituted aliphatic group, an aryl group or a substituted aryl group; said method comprising the steps of:

a) reacting a ketone reducing agent with a diphenyl ketone represented by the following structural formula:

to form an intermediate represented by the following structural formula:

b) reacting the intermediate formed in step a) with one or more Lewis acids to form the 11-aryl-5,6-dihydro-11H-dibenz[b,e]azepine.

7. The method of claim 6 wherein Phenyl Ring A, Phenyl Ring B and Phenyl Ring C are independently unsubstituted or monosubstituted.

8. The method of claim 7 wherein the ketone reducing agent is a hydride reducing agent.

9. The method of claim 8 wherein the hydride reducing agent is sodium borohydride.

* * * * *